United States Patent [19]

Morano et al.

[11] Patent Number: 4,927,637

[45] Date of Patent: May 22, 1990

[54] LIPOSOME EXTRUSION METHOD

[75] Inventors: Jacqueline K. Morano, Mountain View; Francis J. Martin, San Francisco; Martin Woodle, Menlo Park, all of Calif.

[73] Assignee: Liposome Technology, Inc., Menlo Park, Calif.

[21] Appl. No.: 297,946

[22] Filed: Jan. 17, 1989

[51] Int. Cl.$^5$ .............................................. A61K 37/22
[52] U.S. Cl. ..................................... 424/450; 424/1.1; 264/4.3
[58] Field of Search ................... 424/450, 1.1; 264/4.3; 210/500.36

[56] References Cited

U.S. PATENT DOCUMENTS

| | | |
|---|---|---|
| 4,376,059 | 5/1983 | Davis et al. ........................ 424/450 |
| 4,515,736 | 5/1985 | Deamer ............................... 264/4.3 |
| 47,43,375 | 5/1983 | Seita et al. ..................... 210/500.36 |
| 4,752,425 | 6/1988 | Martin et al. ...................... 424/450 |
| 4,781,871 | 11/1988 | West, III et al. .................. 424/1.1 |

Primary Examiner—Ellis P. Robinson
Assistant Examiner—P. L. Prater
Attorney, Agent, or Firm—Peter J. Dehlinger

[57] ABSTRACT

A suspension of heterogeneous size liposomes is passed through a polymer filter having a web-like construction providing a network of interconnected, tortuous-path capillary pores, and a membrane thickness of at least about 100 microns. The processed liposomes have a selected average size less than about 0.4 microns, and a narrow size distribution.

7 Claims, 2 Drawing Sheets

LIPOSOME EXTRUSION METHOD

FIELD OF THE INVENTION

The present invention relates to methods for producing homogeneous-size liposomes in a selected size range between about 0.1 and 0.4 microns.

REFERENCES

1. Gabizon, A., et al, Cancer Res, 43:4730 (1983).
2. Poznansky, M. L., et al, Pharm Revs, 36(4):277 (1984).
3. Szoka, F., et al, Proc Nat Acad Sci (USA), 75:4194 (1978).
4. Szoka, F., et al, Ann Rev Biophys Bioeng, 9:467 (1980).

BACKGROUND OF THE INVENTION

The use of liposomes for drug delivery has been proposed for a variety of drugs, particularly those which are administered parenterally. Liposomes have the potential for providing controlled "depot" release of the administered drug over an extended time period, and of reducing side effects of the drug, by limiting the concentration of free drug in the bloodstream. Liposomes can also alter the tissue distribution and uptake of drugs, in a therapeutically favorable way, and can increase the convenience of therapy, by allowing less frequent drug administration. Liposome drug delivery systems are reviewed in Poznansky.

Generally, the optimal liposome size for use in parenteral administration is between about 0.1 and 0.3, and up to 0.4, microns. Liposomes in this size range can be sterilized by passage through conventional depth filters having particle size discrimination of about 0.2 microns. This size range of liposomes also favors biodistribution in certain target organs, such as liver, spleen, and bone marrow (Gabizon), and gives more uniform and predictable drug-release rates and stability in the bloodstream. Liposomes whose sizes are less than about 0.4 microns also show less tendency to aggregate on storage, and are thus generally safer and less toxic in parenteral use than larger-size liposomes.

A variety of techniques have been proposed for preparing liposomes, including drug-containing liposomes (Szoka, 1980). Typically, these methods yield liposomes which are heterodisperse, and predominantly greater than about 1 micron in size. These initial heterodisperse suspensions can be reduced in size and size distribution by a number of known methods. One size-processing method which is suitable for large-scale production is homogenization. Here the initial heterodisperse liposome preparation is pumped under high pressure through a small orifice or reaction chamber. The suspension is usually cycled through the reaction chamber until a desired average size of liposome particles is achieved. A limitation of this method is that the liposome size distribution is typically quite broad and variable, depending on a number of homogenization cycles, pressures, and internal temperature. Also, the processed fluid has the potential to pick up metal and oil contaminants from the homogenizer pump, and may be further contaminated by residual chemical agents used to sterilize the pump seals.

Sonication, or ultrasonic irradiation, is another method that is used for reducing liposome sizes. This technique is useful especially for preparing small unilameller vesicles (SUVs), in the 0.025-0.08 micron size range. However, a narrow size distribution of liposomes can only be achieved at liposome sizes of about 0.05 microns, i.e., after the liposomes have been reduced to their smallest sizes. The very small liposomes have limited drug carrying or loading capacity and less favorable biodistribution properties than those in the 0.1-0.4 micron size range, as noted below. The processing capacity of this method is also quite limited, since long-term sonication of relatively small volumes is required. Also, heat build-up during sonication can lead to peroxidative damage to lipids, and sonic probes shed titanium particles which are potentially quite toxic in vivo.

A third general size-processing method known in the prior art is based on liposome extrusion through uniform pore-size polycarbonate membranes (Szoka, 1978). This procedure has advantages over the above homogenization and sonication methods in that a variety of membrane pore sizes is available for producing liposomes in different selected size ranges, and in addition, the size distribution of the liposomes can be made quite narrow, particularly by cycling the material through the selected-size filter several times. Nonetheless, the membrane extrusion method has several drawbacks in large-scale processing. For one, the pores in the membrane tend to clog, particularly when processing concentrated suspensions and/or when the liposome sizes are substantially greater than the membrane pore sizes. The clogged membranes cannot be cleared, because the filter housing configuration does not allow back flushing. Replacing the filter is likely to compromise the sterility of the extrusion operation and the membranes cannot be steam-sterilized in place, with a high degree of confidence, due to their inherent fragility. Secondly, the total pore surface area is only about 20% of the total surface area of the membrane, restricting the surface area available for extrusion, and thus limiting total throughput.

Co-owned U.S. Pat. No. 4,737,323 to "Liposome Extrusion Method" describes a method for sizing liposomes by extrusion through an asymmetric ceramic filter. According to one aspect of the invention, a single pass through the filter converts a suspension of heterogeneous size liposomes with a substantial portion having sizes greater than 1 micron to a relatively homogeneous population having sizes less than about 0.4 micron. One or more additional passes through the filter, especially in an inside-to-outside direction, produce a convergence to a final reduced average size and polydispersity. According to another aspect of the invention, it was found that the average size of the extended liposomes was substantially smaller than the rated pore size of the ceramic filter.

Ceramic filter extrusion is advantageous for high-volume processing, since the filter presents a large surface area, and the pore surface area constitutes a major portion of total area. Further the filter is designed for operation at relatively high pressure. In addition, the filter can be backflushed to prevent clogging, and easily sterilized. The method thus overcomes the major limitations of the polycarbonate membrane extrusion method, while producing comparable liposome sizing.

BACKGROUND OF THE INVENTION

It is an object of the invention to provide another filter-extrusion method which overcomes problems and limitations inherent in prior-art polycarbonate-membrane extrusion methods.

A related object of the invention is to provide such a method which yields liposomes having a selected average size less than about 0.4 microns, and a size polydispersity of less than about 0.2 and preferably less than about 0.15 with only a few extrusion passes.

Still another object of the invention is to provide a liposome suspension having a polydispersity of less than about 0.125.

In practicing the method of the invention, a suspension of liposomes containing a substantial portion of liposomes with sizes greater than about 1 micron is passed through a polymer membrane filter characterized by:

(a) a web-like construction providing a network of interconnected, tortuous-path capillaries;

(b) a membrane thickness of at least about 100 microns; and (c) a membrane pore size rating which is approximately the sum as the desired average size of the liposomes.

In one preferred embodiment, the filter is a nylon, polysulfone, or polypropylene membrane having a rated pore size of about 0.2 microns. The extruded liposomes have an average size of between about 0.2 and 0.3 microns. In another embodiment, the filter has a rated pore size of 0.1 micron, and the extruded liposomes have an average size, after 3-5 passes, of about 0.1 micron. Where the filter is a nylon or polysulfone polymer membrane, the polydispersity of the liposomes may be less than about 0.15, and preferably less than about 0.125.

Also disclosed is a suspension of liposomes having a selected average size less than about 0.4 microns and a polydispersity of less than about 0.125. The suspension is formed by providing a suspension of liposomes containing a substantial portion with sizes greater than about 0.4 micron in size and a polydispersity greater than about 0.2, passing the suspension through a polysulfone polymer filter of the type described above, and repeating the extrusion passes until the desired reduction in liposome-size polydispersity is achieved.

These and other objects and features of the present invention will become more fully apparent when the following detailed description of the invention is read in conjunction with the accompanying drawings.

DETAILED DESCRIPTION OF THE INVENTION

A. Preparation of Polydisperse Liposome

Polydisperse, i.e. heterogeneous-size, liposomes, or lipid vesicles, are formed from standard vesicle-forming lipids, which generally include neutral and negatively charged phospholipids and a sterol, such as cholesterol. A variety of lipids having selected acyl chain compositions are commercially available or may be obtained using standard lipid solution procedures.

Several methods for producing a suspension of the heterogeneous-size vesicles are available. In one preferred method, vesicle-forming lipids are taken up in a suitable organic solvent or solvent system, and dried in vacuo or under an inert gas to a lipid film. Where the vesicles are formulated to include a lipophilic or amphiphilic drug, such may be included in the lipids forming the film. To form the vesicles, aqueous medium is added to the dry film, and the film is allowed to hydrate, typically over a one-two hour period with gentle shaking. The lipids hydrate to form multilamellar vesicles (MLVs) whose sizes range typically between about 0.5 microns to about 10 microns or greater. In general, the size distribution of MLVs can be shifted toward slightly smaller sizes by hydrating the lipids under more vigorous shaking conditions. The aqueous medium used in hydrating the lipid film may include a water-soluble drug which then becomes encapsulated in the vesicles which form during lipid hydration.

For producing liposomes under conditions of high encapsulation efficiency, a reverse evaporation phase method is preferred. Reverse-phase evaporation vesicles (REVs) formed by this method are characterized by (a) one or more bilayers, (b) an encapsulation efficiency typically between about 20-50% and (c) a broad spectrum of sizes between about 0.5 and up to 20 microns. These and other liposome-preparation methods have been reviewed (Szoka, 1980).

One preferred liposome processing method is carried out by injecting a lipid-in-Freon TM solution into an aqueous medium, under controlled pressure and solvent-input conditions, until a desired liposome concentration in the aqueous medium is achieved. Example I below describes the preparation of a liposome suspension by the Freon TM -injection method. The liposome suspension has a heterodisperse size distribution of between about 0.1 to 2 microns, with about 15-20% of the liposomes being larger than 1 micron.

B. Sizing Liposomes

According to an important feature of the invention, the heterodisperse liposome suspension produced by above-described methods is passed through a polymer membrane filter of the type described below, to produce liposomes with a desired average size less than 0.4 microns and a desired reduced polydispersity.

Figure 1A:
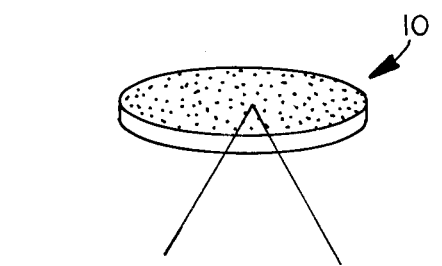
FIG. 1A shows a perspective view of a nylon membrane filter for use in the present invention.
Figures 1B, 1C:
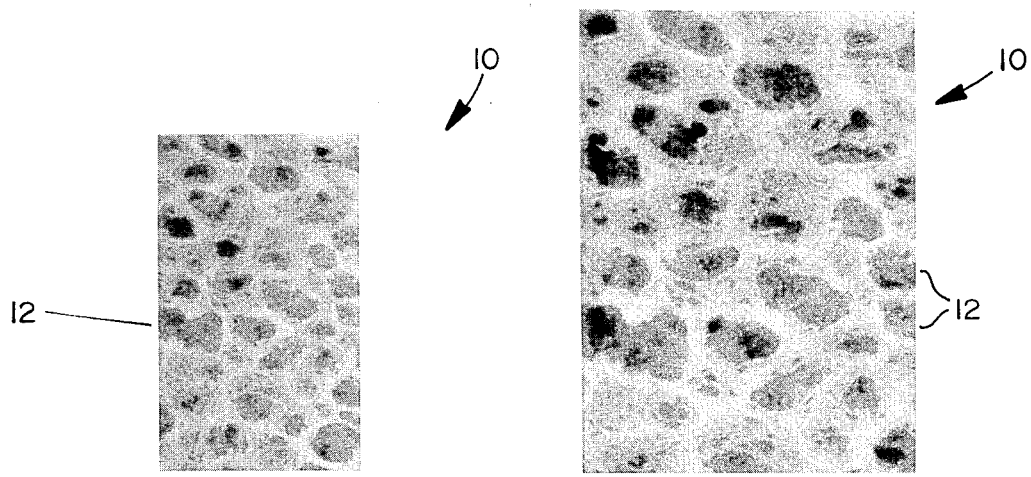
FIGS. 1B and 1C are graphic representations of scanning electron micrographs of a surface portion of a 0.2 micron pore membrane nylon filter at different magnifications.

FIG. 1A shows a 0.2 micron pore nylon membrane filter 10 which is exemplary of the type of filter used in the method. The surface features of the filter are seen in FIGS. 1B and 1C which are graphical representations of different magnification scanning electron micrographs of a surface portion of filter 10. The filter has a web-like structure defining surface pores, such as pores 12, which make up approximately 80% of total membrane surface area.

Figure 2:
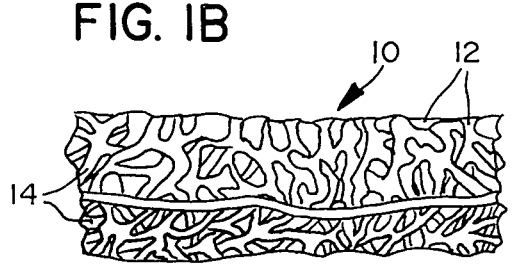
FIG. 2 is a graphic representation of a cross-sectional view of the FIG. 1A filter.

FIG. 2 is an idealized cutaway view of a portion of filter 10, as it might appear at high magnification if the upper surface region of the filter were sliced away. As indicated, the surface pores seen on the surface are part of a network of capillaries, such as capillaries 14, which define tortuous capillary paths through the filter. That is, material which enters the filter through the surface pores must travel from one capillary to another along a tortuous path in traversing the membrane. The thickness of the membrane is typically about 150 microns, and at least about 100 microns. The filter shown in the figures has an unsupported construction, and must therefore be mounted on a filter support, as described below. The filters may also be supplied with a web-like polymer support which is formed integrally to the filter.

Figures 3, 4:
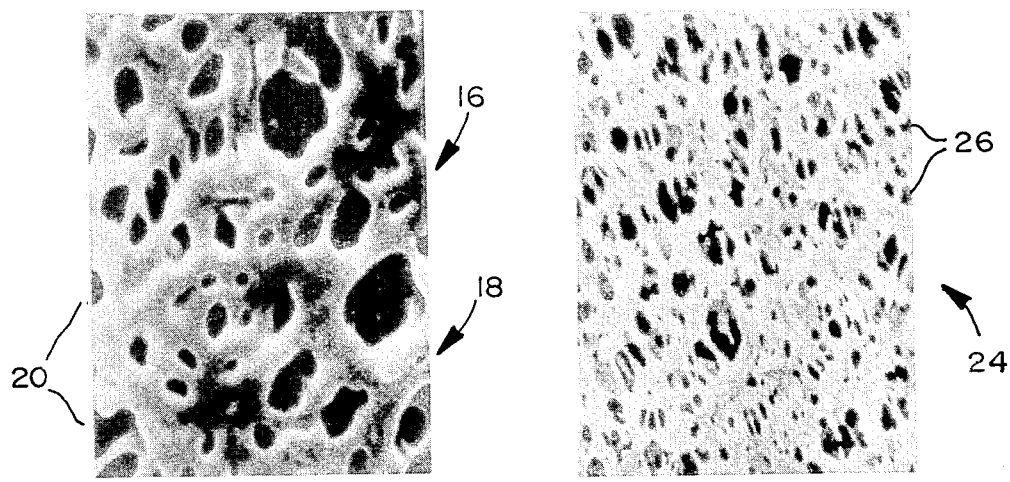
FIG. 3 is a scanning electron micrograph of a surface portion of a 0.2 micron pore polysulfone membrane filter.
FIG. 4 is a scanning electron micrograph of a surface portion of a 0.2 micron pore polypropylene membrane filter.

FIG. 3 is a representation of a scanning electron micrograph of the surface region 16 of a polysulfone membrane 18 also applicable to the present invention. As seen, the membrane has the general web-like construction of the FIG. 1 nylon filter, defining an array of surface pores, such as pores 20, and a network of interconnected, tortuous-path capillaries, similar to that shown in FIG. 2. The thickness of the membrane is preferably about 150 nm, and at least about 100 nm.

FIG. 4 shows a similar magnified-surface portion of a polypropylene membrane 24 also applicable to the invention. As above, this membrane is characterized by a general web-like construction, having an array of surface pores, such as pores 26, a network of interconnected, tortuous-path capillaries, such as shown in FIG. 2, and a membrane thickness preferably about 150 nm, and at least about 100 nm. In each of the polymer filters described above, the rated pore size of the filter, i.e., the size of solid particles which are excluded by the filter, is determined by the cross-sectional area of the tortuous-path capillaries in the membrane, e.g., 0.2 microns. According to one aspect of the invention, the average size of liposomes produced by extrusion through the membrane is about the same as or slightly larger than, the filter's rated pore size. Thus, as shown in Example II below, filtration of heterogeneous size liposomes through a 0.2 micron (200 nm) nylon filter produces liposomes having an average size in the size range between about 220–260 nm; through a 0.2 micron polysulfone membrane, an average size in the size range between about 240–280 nm; through a 0.2 micron polypropylene membrane, an average size in the size range between about 215–220 nm; and through a 0.1 micron polypropylene membrane, an average size in the size range between about 100–150 nm, where the smaller average sizes are achieved after 3–5 passes through the membrane.

According to another feature of the invention, the liposome size distribution after extrusion can be made exceptionally narrow, as judged by a standard deviation of less than about 30%, and a polydispersity of sizes between about 0.1–0.2, and often less than about 0.125–0.15. Although standard deviation and polydispersity do not precisely define the shape of the size distribution curve for a non-Gaussian distribution of particle sizes, the parameters do provide a good measure of size homogeneity. A polydispersity of less than 0.1 indicates virtually uniform sizes, such as controlled size latex particles; a polydispersity of between about 0.1 and 0.125 represents a high degree of particle-size uniformity; a polydispersity between 0.15–0.2, moderate-to-high homogeneity; and greater than about 0.25, a fairly broad size distribution. The method of calculating polydispersity from the measured sizes of particles in a mixed-particle suspension is described below in Section C.

The standard deviation and polydispersity of liposome sizes after extrusion through nylon, polysulfone, and polypropylene membranes are given in Tables I, II, and III, respectively, in Example 2. After a single pass through each of these filters, polydispersity is reduced from about 0.26 to about 0.18, and with 3–5 passes, polydispersity is typically less than about 0.15. Lower polydispersity is achieved with nylon and polysulfone filters, consistent with the standard deviation data, where values of less than 30% standard deviation are seen after three passes through nylon or polysulfone filters.

Figure 5:
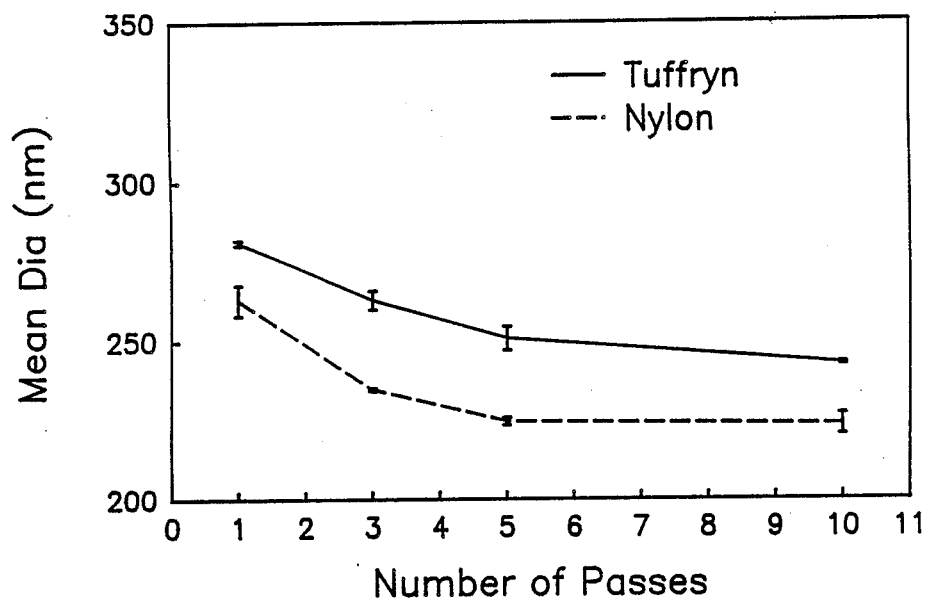
FIG. 5 is a plot showing change in liposome average size, as a function of number of extrusion passes through a nylon (dashed line) or polysulfone (solid line) membrane filter.
Figure 6:
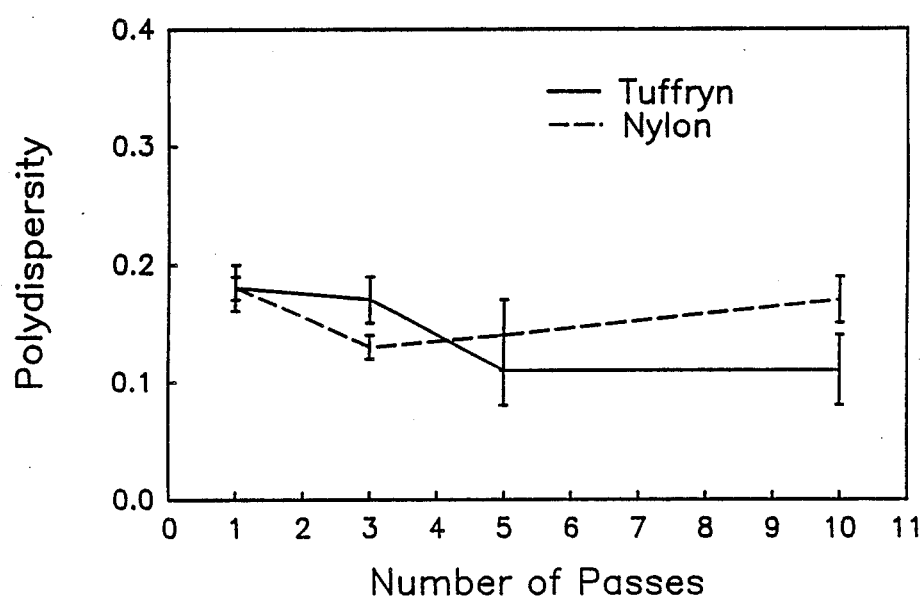
FIG. 6 is a plot showing change in liposome size polydispersity, as a function of number of extrusion passes through a nylon (dashed line) or polysulfone (solid line) membrane filter.

Another important feature of the method is the rapid convergence of liposome size and polydispersity, after only 1 pass through the polymer membrane, and the nearly complete convergence after 3–5 passes. This feature is seen in FIGS. 5 and 6, which show changes in mean diameter and polydispersity as a function of number of passes through nylon (dashed lines) and polysulfone (solid lines) filters. A single pass through either a nylon or polysulfone membrane reduced liposome mean diameter to within about 17% of its final value, achieved after 3–5 passes. Polydispersity is similarly reduced from greater than 0.25 to about 0.18 or less by a single pass, with rapid convergence to a stable polydispersity within 3–5 passes.

Summarizing, the polymer membranes which are useful in the method are characterized by (a) a web-like construction providing a network of interconnected, tortuous-path capillaries; (b) a membrane thickness of at least about 100 microns; and (c) a membrane pore size rating which is approximately the same as the desired average size of the liposomes.

In a typical liposome sizing operation, a selected polymer membrane filter is placed in a suitable filtration device which forms a fluid-tight seal at the filter, and which can withstand relatively high filtration pressures, such as 250 psi, applied to the liquid above the filter. One exemplary filtration system is described in Example 2.

Alternatively, a filtration system like that described in U.S. Pat. No. 4,737,323 may be employed, using a filter device capable of supporting a membrane filter from both sides. Here the filter device is suitably connected between two pressure chambers, and the suspension extruded from one vessel to the other, alternately in different directions through the filter. Cycling the material alternatively in a back direction reduces particle build-up and clogging at the filter surfaces.

The size processed liposome suspension may be readily sterilized by passage through a sterilizing membrane having a particle discrimination size of about 0.2 microns, such as a conventional 0.22 micron depth membrane filter.

Where liposomes are formulated to contain an entrapped drug, for use in parenteral drug administration, it is usually advantageous to further process the sized liposomes to remove free drug, i.e., drug present in the bulk aqueous phase of the suspension. This is done to reduce the effects of free drug and to maximize the benefits achievable by drug entrapment in the liposomes. Methods for removing free drug from liposome suspensions are well-known.

C. Homogeneous Liposome Suspension

In another aspect, the invention includes a suspension of sized liposomes having a polydispersity of no greater than about 0.125. Polydispersity, as defined herein, is a dimensionless size-distribution measure related to standard deviation of sizes in a mixed-particle suspension. It is calculated, formally, by the following equation:

$$\text{Polydispersity} = 1 - (\text{1st moment}/\text{2nd moment})^2,$$

where the first and second moments are the first and second apparent average sizes, respectively, measured in the sample by a dynamic light scattering instrument. Note that the second apparent average size is always larger than the first, so that as the second approaches the first, the polydispersity approaches zero.

Generally, the polydispersity calculation is performed automatically by a microprocessor associated with a conventional laser particle-size discriminator, such as the one used in obtaining the data presented in Example 2.

The low-dispersity suspension is formed, in accordance with the invention, by forming a liposome suspension having an average size greater than about 0.4 microns and a polydispersity substantially greater than 0.125, e.g., greater than about 0.18. Typically, the suspension will be an unsized liposome suspension prepared by one of the methods below. Alternatively, some presizing, for example by mild homogenation, may be used to reduce liposome sizes initially.

The suspension is then passed through a nylon or polypropylene membrane of the type described above, i.e., characterized by: (a) a web-like construction providing a network of interconnected, tortuous-path capillary pores; (b) a membrane thickness of at least about 100 microns; and (c) a membrane pore size rating which is approximately the same as the desired average size of the liposomes. The membrane extrusion step is repeated, typically for a total of 3-5 passes, until the desired reduction in liposome-size polydispersity is achieved.

D. Utility

Sized liposome suspensions prepared according to the invention are useful in a variety of liposome therapeutic compositions in which controlled sizes between about 0.1 and 0.3 microns are desired. One important class of compositions includes drug-containing liposomes for parenteral drug administration. As indicated above and reviewed extensively in the Poznansky reference, liposomal drug-delivery systems have been developed and tested with a wide range of water-soluble and lipid-soluble drugs. Although many of the earlier proposed liposome/drug systems were not carefully defined in terms of size, a variety of experimental evidence and practical considerations indicate advantages of the 0.1 to 0.3 micron size range. In particular, this size range is generally preferred to larger-size liposomes because of ease of sterilization, improved biodistribution, and reduced tendency to aggregate on storage.

From the foregoing, it can be appreciated how various objects of the invention are met. The liposome processing method yields liposome sizes in a selected size range of between about 0.1 and 0.4 microns, and with a narrow distribution of sizes.

The method is well suited to a high throughput liposome processing operation due in part to the relatively high pressure which may be used, and in part to the high surface area of the membrane pores. Throughput may also be increased by bidirectional extrusion, which acts to prevent membrane clogging. The method generates very little heat, and can be performed under aseptic conditions.

The system is reliable and requires very little maintenance, due to the durability of the membranes and ability to sterilize the membranes in the filter system. Specifically, selected polymer filters can be sterilized by dry heat at temperatures up to 100° C., and/or selected for resistance to solvents, such as oxidizing agents, effective for chemical sterilization.

The following examples illustrate both use and results achievable with the method of the invention, but are in no way intended to limit the scope of the invention.

EXAMPLE I

Preparation of Heterogeneous-Size Liposomes

Egg phosphatidylcholine (EPC) was obtained from Asahi Lipids (Japan); egg phosphatidylglycerol (EPG), from Avanti Lipids (Birmingham, AL), and cholesterol, from Croda.

EPC (88.5 moles), EPG (1.5 moles), and cholesterol (60 mmoles) were dissolved in 375 ml of Freon-11 TM, giving a final lipid concentration of about 400 mM. The lipid solution was injected into 1.5 l of .09% saline, pH 6.0, at a rate of about 40 ml/min, under a vacuum which was adjusted to maintain total suspension volume substantially constant, i.e., the Freon TM solvent was removed at about 40 ml/min. The temperature of the solvent and aqueous medium were maintained at 20° C. during liposome formation.

To determine the size distribution of the liposomes, an aliquot of the above suspension was centrifuged at 10,000×g for 10 minutes, and the pelleted liposomes and supernatant were separately analyzed by a combination instrument: a Nicomp Laser Particle-Size Discriminator, Model No. 200 with a Brookhaven instrument BI2030 AT Correlator. The pellet, which contained about 67% of the total liposome fraction by lipid mass, contained about 74% liposomes less than 1 micron, about 24% between 1-2 microns, and about 2% greater than 2 microns. Thus, the suspension contained about 17% by mass liposomes with sizes greater than about 1 micron. The supernatant, which contained about 33% of the suspension liposomes by mass had an average size of about 377 nm, and a polydispersity of about 0.26.

EXAMPLE II

Liposome Sizing By Polymer Membrane Filters

Nylon and polypropylene unsupported membrane filters were supplied by Setec (Livermore, CA); and polysulfone unsupported membranes, from Gelman Sciences (Ann Arbor, MI). The membranes were either supplied at 25 mm or cut to this size. Rated pore sizes of the membranes were 0.2 or 0.1 microns, as indicated in the table below.

The membranes were placed in a high-pressure extrusion device in which the membrane filters are supported on a porous stainless steel support and liquid was forced through the filter by pressure applied above the liquid. Extruded suspension volumes were about 10 ml and the applied pressure was about 250 psi. The suspension was passed through a filter a total of ten times. After 1-10 passes, an aliquot of the material was removed and particle size distribution was analyzed by laser particle discrimination as in Example 1. The size analysis yielded Gaussian mean diameter (nm), standard deviation (%), average effective diameter (nm) and polydispersity.

Table I shows the size distribution characteristics of the liposome suspension after 1, 3, 5, and 10 passes through a 0.2 micron nylon filter. The final average effective size of about 224 nm is approximately equal to the rated pore size of the membrane. The size and polydispersity of the suspension, as a function of number of passes, show little change after 3–5 passes (FIGS. 5 and 66, dashed line).

TABLE I

| Pass No. | Gaussin Mean Diam. (nm) | Std. Dev. (%) | Avg. Eff. Diam. (nm) | Poly-Dispersity |
|---|---|---|---|---|
| 1 | 278.8 | 33 | 263.3 | .181 |
| 3 | 247.4 | 29 | 235.2 | .125 |
| 5 | 238.8 | 28 | 224.5 | .139 |
| 10 | 235.6 | 31 | 224.4 | .166 |

Table II shows size data for extrusion of the suspension through a 0.2 micron polysulfone filter. The data is comparable to that seen with the nylon filter, although average liposome effective sizes are slightly greater. As seen in FIG. 5 (solid line) mean effective size stabilized after 5 passes, similar polydispersity (FIG. 6, solid line) was stabilized after 5 passes.

TABLE II

| Pass No. | Gaussin Mean Diam. (nm) | Std. Dev. (%) | Avg. Eff. Diam. (nm) | Poly-Dispersity |
|---|---|---|---|---|
| 1 | 299.5 | 37 | 280.7 | .185 |
| 3 | 278.1 | 28 | 262.9 | .168 |
| 5 | 262.7 | 27 | 250.7 | .106 |
| 10 | 252.7 | 27 | 242.5 | .109 |

Table III shows size data for extrusion of the suspension through a 0.2 micron polypropylene filter. The size data is similar to that seen with the nylon and polysulfone filters, showing average effective sizes of about 220 nm for a single pass, and slight size reduction down to about 215 nm with 5 passes. No appreciable change in mean effective size (about 215 nm) or polydispersity is observed after about 3 passes.

TABLE III

| Pass No. | Gaussin mean Diam. (nm) | Std. Dev. (%) | Avg. Eff. Diam. (nm) | Poly-Dispersity |
|---|---|---|---|---|
| 1 | 257.0 | 51 | 223.0 | .183 |
| 2 | 234.1 | 34 | 223.8 | .146 |
| 3 | 223.5 | 35 | 214.1 | .111 |
| 4 | 225.5 | 36 | 216.9 | .150 |
| 5 | 224.9 | 35 | 215.3 | .145 |

Extrusion through a 0.2 micron polypropylene membrane filter for 10 passes gave the size distribution data seen in Table IV. The data shows little reduction in mean size or polydispersity between passes 1 and 10. Table V shows size characteristics after up to 10 passes through a 0.1 micron polypropylene filter. It is noted that liposome sizes after 5–10 passes are close to the rated filter pore size.

TABLE IV

| Pass No. | Gaussin Mean Diam. (nm) | Std. Dev. (%) | Avg. Eff. Diam. (nm) | Poly-Dispersity |
|---|---|---|---|---|
| 1 | 240.1 | 34 | 230.0 | .181 |
| 3 | 240.8 | 37 | 229.8 | .202 |
| 5 | 240.3 | 37 | 228.4 | .188 |
| 10 | 218.0 | 33 | 209.4 | .173 |

TABLE V

| Pass No. | Gaussin Mean Diam. (nm) | Std. Dev. (%) | Avg. Eff. Diam. (nm) | Poly-Dispersity |
|---|---|---|---|---|
| 1 | 151.9 | 31 | 152.0 | .159 |
| 3 | 130.5 | 35 | 137.0 | .177 |
| 5 | 115.9 | 36 | 123.4 | .223 |
| 10 | 99.2 | 30 | 105.4 | .161 |

EXAMPLE III

Comparison of Polymer and Scintered Steel Membrane Extrusion

A suspension of liposomes prepared as in Example 1 were extruded through 0.2 micron stainless steel porous membrane filter obtained from Mott (Farmington, CT). These membranes are formed by scintering metal fragments, giving a tortuous-path filter construction whose pore size (size of particles filtered) is determined by the sizes of metal particles making up the filter. Filtration conditions were as described in Example 2.

The size distribution characteristics of the liposomes after up to 10 passes are given in Table VI below.

TABLE VI

| Pass No. | Gaussin Mean Diam. (nm) | Std. Dev. (%) | Avg. Eff. Diam. (nm) | Poly-Dispersity |
|---|---|---|---|---|
| 1 | 454.8 | 49 | 427.3 | .264 |
| 3 | 397.4 | 44 | 380.0 | .252 |
| 5 | 373.6 | 43 | 356.3 | .229 |
| 10 | 318.1 | 41 | 302.5 | .216 |

One pass through the filter produced little change in the mean size and polydispersity of the unextruded liposome suspension. Even after 10 passes, the polydispersity of the filtered material was quite high and liposome mean sizes were substantially larger than the rated pore size.

The sizing effect produced by scintered steel membranes contrasts with that produced by polymer membranes.

While preferred embodiments of the invention have been described herein, it will be apparent to those skilled in the art that various changes and modifications can be made without departing from the invention.

It is claimed:

1. A method of producing a suspension of liposomes which have uniform sizes and a selected average size in the size range between about 0.1 and 0.4 microns, said method comprising
providing a suspension of heterogeneous-size liposomes containing a substantial portion with sizes greater than 1.0 micron, and
passing the suspension through a polymer membrane filter characterized by:

(a) a web-like construction providing a network of interconnected, tortuous-path capillary pores;
(b) a membrane thickness of at least about 100 microns; and
(c) a membrane pore size rating which is approximately the same as the selected average size of the liposomes.

2. The method of claim 1, wherein the polymer forming the filter is selected from the group consisting of polysulfone, nylon, and polypropylene.

3. The method of claim 1, for producing a suspension of liposome having a selected average size between about 0.2 and 0.3 microns, wherein the rated pore size of the filter is 0.2 microns.

4. The method of claim 1, for producing a suspension of liposome having a selected average size between about 0.1 and 0.15 microns, wherein the rated pore size of the filter is 0.1 microns.

5. The method of claim 1, for producing a suspension of liposome having a polydispersity no greater than about 0.125, wherein the filter is a polysulfone filter having a rated pore size of 0.1 or 0.2.

6. A method of producing liposomes having a selected average size of no greater than about 0.4 microns and a polydispersity of no greater than about 0.125, comprising
providing a dispersion of liposomes containing a substantial portion with sizes greater than 0.4 microns and a polydispersity greater than about 0.18,
passing the suspension through a polysulfone membrane filter characterized by
(a) a web-like construction providing a network of interconnected, tortuous-path capillary pores;
(b) a membrane thickness of at least about 100 microns; and
(c) a membrane pore size rating which is approximately the same as the desired average size of the liposomes, and
repeating said passing step 2–4 times until the desired polydispersity is achieved.

7. The method of claim 6, wherein the dispersion provided has a substantial portion of liposome sizes greater than about 1 micron, and a polydispersity greater than about 0.25.

* * * * *

UNITED STATES PATENT AND TRADEMARK OFFICE
CERTIFICATE OF CORRECTION

PATENT NO. : 4,927,637

DATED : May 22, 1990

INVENTOR(S) : J. Morano, F. Martin, M. Woodle

It is certified that error appears in the above-identified patent and that said Letters Patent is hereby corrected as shown below:

Column 4, line 14, replace solution with --isolation--.

Signed and Sealed this

Eleventh Day of June, 1991

Attest:

HARRY F. MANBECK, JR.

Attesting Officer

Commissioner of Patents and Trademarks